United States Patent [19]

Mersch

[11] Patent Number: 5,776,129
[45] Date of Patent: Jul. 7, 1998

[54] ENDOMETRIAL ABLATION APPARATUS AND METHOD

[75] Inventor: Steven H. Mersch, Germantown, Ohio

[73] Assignee: Ethicon Endo-Surgery, Inc., Cincinnati, Ohio

[21] Appl. No.: 662,892

[22] Filed: Jun. 12, 1996

[51] Int. Cl.$^6$ .................................................. A61B 17/38
[52] U.S. Cl. .............................. 606/31; 606/13; 606/15; 606/18
[58] Field of Search .................. 606/15, 16, 28, 606/17, 18, 2, 10–13, 31, 27; 607/89, 92, 93

[56] References Cited

U.S. PATENT DOCUMENTS

| 4,612,938 | 9/1986 | Dietrich et al. | 606/12 |
|---|---|---|---|
| 4,662,383 | 5/1987 | Sogawa et al. | 128/784 |
| 4,676,258 | 6/1987 | Inokuchi et al. | 128/804 |
| 4,799,479 | 1/1989 | Spears | 606/15 |
| 4,979,948 | 12/1990 | Geddes et al. | 606/33 |
| 5,045,056 | 9/1991 | Behl | 604/49 |
| 5,277,201 | 1/1994 | Stern | 607/41 |
| 5,395,361 | 3/1995 | Fox et al. | 606/16 |
| 5,449,354 | 9/1995 | Knowitz et al. | 606/15 |

FOREIGN PATENT DOCUMENTS

| 2000189 | 4/1990 | Japan | 607/89 |
|---|---|---|---|
| WO 95/07664 | 3/1995 | WIPO | |
| 95/k13026 | 5/1995 | WIPO | |

OTHER PUBLICATIONS

"Lumitex® Creators of Woven Light" Catalogue, dated Apr. 1995, for woven fiber optic lighting products for LCD's, membrane switches, automative and other applications.
"Gynaecological Endoscopy" vol. 4, Supplement 1, Dec. 1995, Abstract 036.
Back lighting with plastic optical fiber devices, Poly–Optical, Poly–Optical Products, Inc.

*Primary Examiner*—John P. Lacyk
*Assistant Examiner*—Rosiland Kearney
*Attorney, Agent, or Firm*—Bernard Shay

[57] ABSTRACT

A method of performing endometrial ablation comprising heating entire surface of the endometrium to a temperature of between 45° C. and 70° C. to destroy the cells of the endometrial lining while maintaining the average temperature of the myometrium at a temperature below approximately 42° C. An apparatus for performing an endometrial ablation comprising an expandable membrane such as a balloon adapted to fit within the uterus and contact the endometrial lining when expanded. A web of light diffusing fiber-optic cables arranged on the outer surface the balloon such that the web contacts the endometrial lining of the uterus when the balloon is expanded. The fiber-optic web is connected to an array of high intensity lamps via a series of fiber-optic cables. The temperature of the endometrium is monitored by a of a series of temperature sensors arranged upon the surface of the balloon.

3 Claims, 10 Drawing Sheets

ENDOMETRIAL ABLATION APPARATUS AND METHOD

FIELD OF THE INVENTION

The present invention relates to a method and apparatus for the destruction of the inner lining of body organs, and, more particularly, to a method and apparatus for the selective destruction of the endometrium.

BACKGROUND OF THE INVENTION

In certain circumstances it may be advantageous to destroy one or more layers of the inner lining of various body organs. Such destruction may be advantageous in the treatment or prevention of certain diseases or other physical conditions. In particular, dysfunctional uterine bleeding (DUB) which can be a problem for many women, and particularly for postmenopausal women. Various methods and apparatus have been used to destroy layers of living tissue without damaging the underlying layers. Some of the apparatus include devices for heating the layer to be destroyed using, for example, radio frequency energy and microwave energy. Alternatively, other thermal techniques for destroying the inner lining of various body organs include chemical treatments, cryotherapy, laser therapy and electrosurgery.

U.S. Pat. No. 5,277,201 describes a method and apparatus for endometrial ablation utilizing an electrically conductive balloon adapted to supply Monopolar RF energy to the endometrial layer when the balloon is expanded within the body organ. U.S. Pat. No. 5,277,201 further illustrates a balloon device for use in endometrial ablation wherein the balloon surface includes a plurality of selectively excitable RF electrodes along with a plurality of selectable temperature sensors adapted to measure the temperature of the endometrium during the ablation process. U.S. Pat. No. 4,979,948 describes thermal ablation of the mucosal layer of a gallbladder by resistive heating with an RF balloon electrode. Electric current is delivered via a conductive expansion liquid which fills the balloon. Balloon catheters supplied with a heated fluid have also been used for thermal ablation of hollow body organs as described in U.S. Pat. No. 5,045,056. Application of microwave and high frequency RF energy to destroy tissue, using electrodes enclosed in expanded balloons have been described in, for example, U.S. Pat. Nos. 4,662,383 and 4,676,258.

SUMMARY OF THE INVENTION

According to the present invention, an apparatus for heating tissue in the interior of a body organ, for example the uterus, comprises an expandable element adapted to fit within the body organ wherein the expandable element is covered with a web of optically conductive material arranged to conduct light to the interior surface of the body organ. In this embodiment, the expandable element may include a reflective surface which reflects light from the optically conductive material to the interior surface of the body organ.

In one embodiment of the present invention, the web of optically conductive material may be, for example, a web of optical fibers connected to one or more light sources, for example high intensity lamps or lasers, which generate the light energy transmitted by the optically conductive material. In a further embodiment of the present invention, temperature detection devices, for example thermocouples, are attached to the expandable element to measure the temperature of the lining of the body organ as it is being heated by the light energy transmitted by the optically conductive material.

The present invention further includes a method of selectively heating the lining of a body organ utilizing the apparatus of the present invention including the steps of inflating the expandable element to fit within the body organ, heating the interior surface of the body organ by passing light energy from the light source through the optically conductive material to the lining. In addition, a method according to the present invention may include the step of measuring the temperature of the lining and selectively turning the light sources on and off to control the temperature of the lining.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

Figures 1, 2:
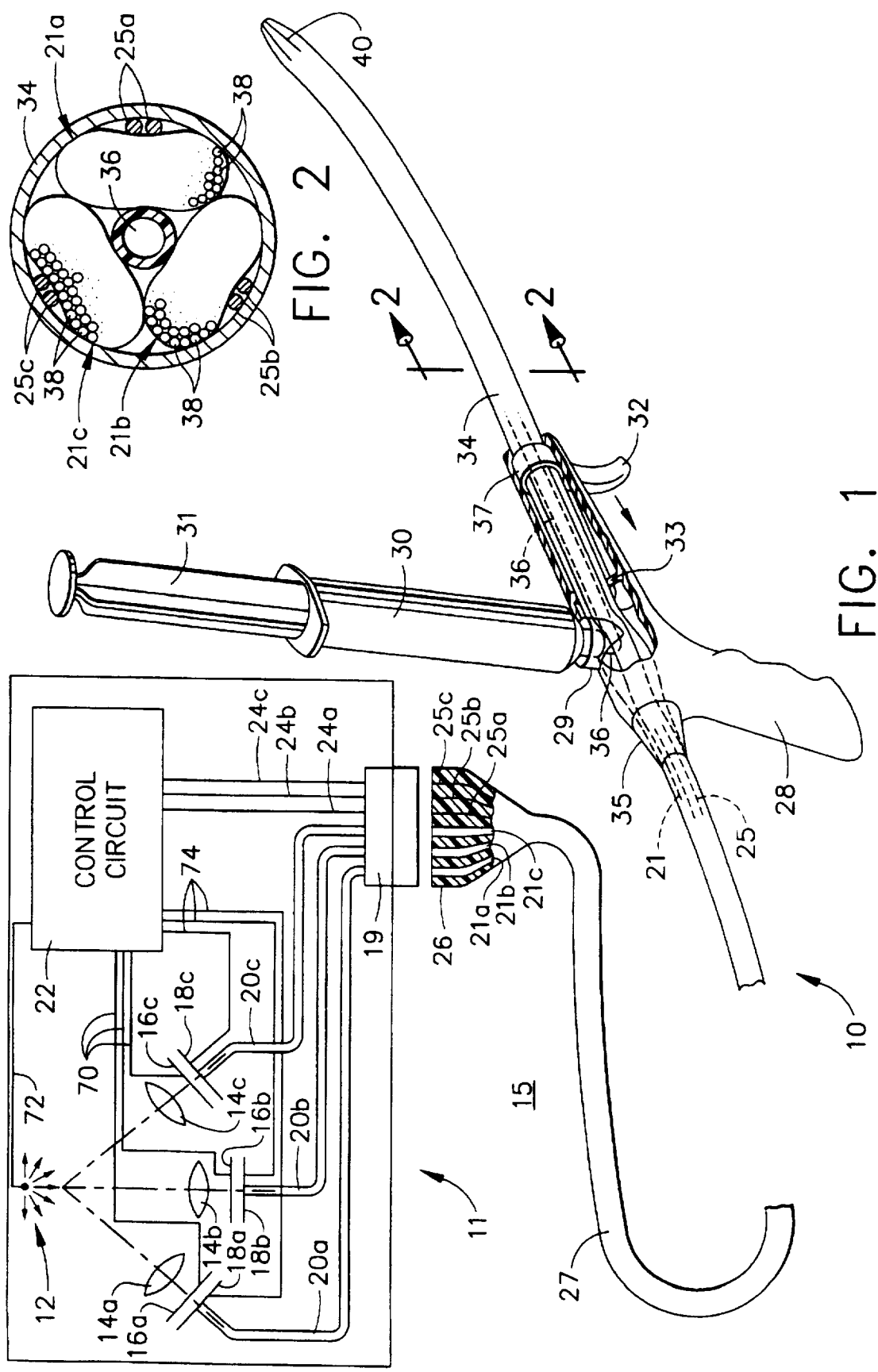
FIG. 1 illustrates an optical ablation system according to the present invention including an ablation instrument and an electro-optic generator.
FIG. 2 is a cross sectional view of the ablation instrument illustrated in FIG. 1 along view line 2—2.

FIG. 1 illustrates an optical ablation system 15 according to the present invention including an ablation instrument 10 and an electro-optic generator 11. In FIG. 1. Optical Energy in the form of light is supplied to ablation instrument 10 by electro-optical generator 11. As used herein, the term "optical" is intended to include that portion of the electromagnetic spectrum including radiation in the ultraviolet, visible and infrared wavelengths. Electro-optical generator 11 includes an optical energy source 12, one or more energy coupling devices 14, one or more optical filters 16, one or more variable attenuators 18 which may also comprise a variable neutral density filter, one or more fiber optic bundles 20, one or more thermocouple inputs 24 and control circuitry 22. Optical energy source 12 may be, for example, a laser, a halogen lamp, a conventional incandescent lamp or other optical energy source. Optical energy source 12 may be a single source which provides light which is white or spectrally pure at a specific wavelength. Alternatively, Optical energy source 12 may include a plurality of light sources having any combination of wavelengths and power levels. Optical energy source 12 is coupled to fiber optic bundle 20 by energy coupling lens 14, optical filter 16 and variable attenuator 18.

Energy coupling lens 14 focuses optical energy from optical energy source 12 through optical filter 16 and variable attenuator 18 onto the proximal end of fiber optic bundle 20. The intensity and/or wavelength of optical energy source 12 may be controlled by, for example, signals from control circuit 22 transmitted through control line 72. Optical filter 16 may be a single frequency filter adapted to filter out all but one of the wavelengths generated by optical energy source 12. Alternatively, Optical filter 16 may be a plurality of selectable filters from which a filter effective at one or more wavelengths may be chosen to selectively filter optical energy generated by optical energy source 12. Optical filter 16 may also be a spectral filter adapted to pass energy within a band of wavelengths. Optical filter 16 may also be a filter wheel which contains a number of band pass filters. The wavelength of light filtered by optical filter 16 may be controlled by, for example, signals from control circuit 22 transmitted through control line(s) 70. After passing through optical filter 16, energy from optical energy source 12 passes through variable attenuator 18. Variable attenuator 18 may also be referred to as a variable neutral density filter. Variable attenuator 18 is adapted to control the energy level of the light which is focused on to the proximal end of fiber optic bundle 20. The setting of variable attenuator 18 may be controlled by, for example, signals from control circuit 22 transmitted through control line(s) 74. The energy passed by variable attenuator 18 may be controlled by signals from control circuit 22 to ensure that the appropriate energy level is input to the proximal end of fiber optic bundle 20.

Energy coupling lens 14 may include a plurality of energy coupling lenses, for example the three energy coupling lenses 14a, 14b and 14c illustrated in FIG. 1. Optical filter 16 may include a plurality of optical filters, for example, the three optical filters 16a, 16b and 16c illustrated in FIG. 1. Variable attenuator 18 may include a plurality of variable attenuators, for example, the three variable attenuators 18a, 18b and 18c illustrated in FIG. 1. In addition, fiber optic bundle 20 may include a plurality of fiber optic bundles, for example, the three fiber optic bundles illustrated in FIG. 1. The number of energy coupling lenses, optical filters, variable attenuators and fiber optic bundles will depend upon the design of the ablation system 15, however, the number of coupling lenses, optical filters, variable attenuators and fiber optic bundles will generally correspond to the number of regions the ablation instrument is designed to separately heat within the body cavity being treated.

Electro-optic generator 22 includes temperature signal wires 24 which are adapted to relay signals representative of the temperature at selected points at the distal end of ablation instrument 10 to control circuit 22. The number of temperature signal wires 24 will depend upon the design of ablation system 15, however, the number of thermocouple inputs will generally correspond to a multiple of the number of regions the ablation instrument is designed to separately heat. In the embodiment of the ablation instrument illustrated in FIG. 1, the electro-optic generator includes three temperature signal wires 24a, 24b and 24c. In one embodiment of the present invention, temperature signal wires 24 comprise a pair of wires which are connected through ablation instrument 10 to a thermocouple at a distal end of the ablation instrument.

Fiber optic bundles 20 and temperature signal wires 24 terminate at generator connector 19 which is adapted to mate with instrument connector 26. In FIG. 1, instrument connector 26 is shown in cutaway view to show fiber optic bundles 21a, 21b and 21c and to show thermocouple inputs 25a, 25b and 25c which are positioned within instrument connector 26 and flexible sleeve 27. Fiber optic bundles 20 exit electro-optic generator 11 at generator connector 19 where each fiber optic bundle 20a, 20b and 20c is butt-coupled to a corresponding fiber optic bundle 21a, 21b and 21c such that optical energy is transmitted from fiber optic bundles 20a, 20b and 20c to fiber optic bundles 21a, 21b and 21c, respectively. Temperature signal wires 24 also exit electro-optic generator 11 at generator connector 19 where temperature signal wires 24a, 24b and 24c are connected to temperature signal wires 25a, 25b and 25c, respectively. Fiber optic bundles 21 and temperature signal wires 25 pass through flexible sleeve 27 to instrument handle 28 and through instrument handle 28 to rigid sleeve 34.

Instrument handle 28 includes connector 35, fluid source connector 29, sleeve retractor 32, sleeve retractor stop 33 and fluid line 36. Flexible sleeve 27, terminates at connector 35 while fiber optic bundles 21 and temperature signal wires 25 pass through connector support 27 and the central portion of instrument handle 28 to the central annulus of rigid sleeve 34. Fluid source connector 29, which is adapted to receive a fluid source such as, for example, syringe 30, is connected to fluid line 36. In the embodiment of FIG. 1, syringe 30 includes plunger 31 which is adapted to force fluid, for example air, through fluid line 36. Fluid line 36 extends from fluid source connector 29 to the annulus of rigid sleeve 34.

In instrument handle 28 as illustrated in FIG. 1, sleeve retractor 32 is connected to sleeve collar 37 which is connected to rigid sleeve 34 such that rigid sleeve 34 may be retracted in the proximal direction by moving sleeve retractor 32 in the proximal direction. The travel of sleeve retractor 32 is limited by sleeve retractor stop 33, thus limiting the proximal travel of rigid sleeve 34. As rigid sleeve 34 is retracted, expandable sleeve tip 40 at the distal end of rigid sleeve 34 opens, releasing the balloon or other device positioned in the central annulus of rigid sleeve 34 at the distal end of sleeve 34.

FIG. 2 is a cross sectional view of the ablation instrument illustrated in FIG. 1 along view line 2—2. In FIG. 2, fluid line 36 is surrounded by fiber optic bundles 21a, 21b and 21c and by temperature signal wires 25a, 25b and 25c. As illustrated in FIG. 2, fiber optic bundles 21a, 21b and 21c each include one or more fiber optic fibers 38 which are adapted to transmit optical energy. Temperature signal wires 25 are adapted to transmit signals representative of temperature. Fluid line 36 is adapted to transmit fluid such as, for example, air.

Figure 3:
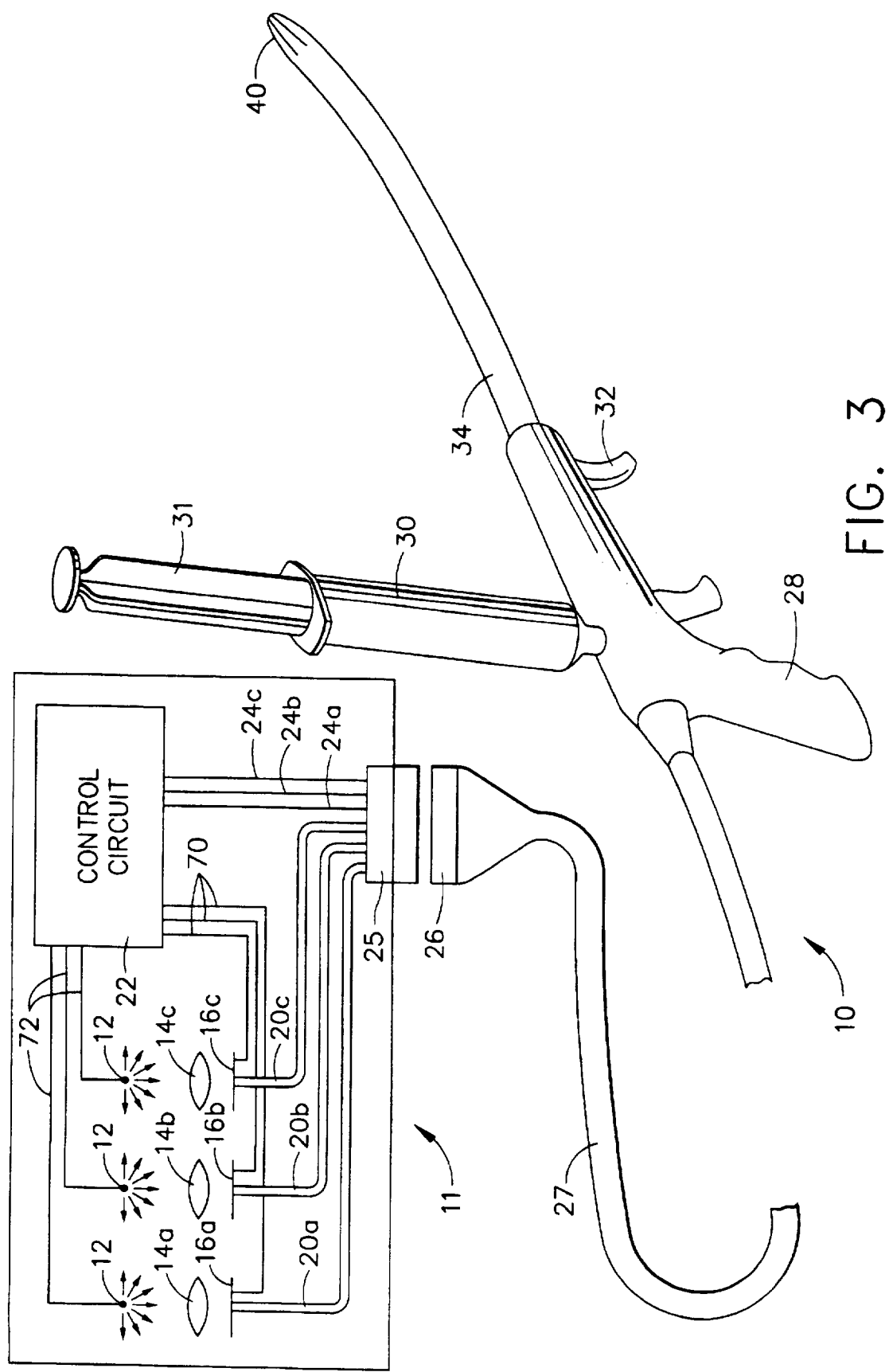
FIG. 3. illustrates an optical ablation system according to the present invention including an ablation instrument and an alternative embodiment of an electro-optic generator.

FIG. 3 illustrates an optical ablation system according to the present invention including an ablation instrument and an alternative embodiment of an electro-optic generator. In the embodiment of electro-optic generator 11 illustrated in FIG. 3, optical energy source 12 of FIG. 1 is divided into a plurality of controllable optical energy sources 12a, 12b and 12c. In one embodiment of the present invention, the intensity of optical energy sources 12 is controllable and the energy from optical energy sources 12a, 12b and 12c is controlled by energy control signals from control circuit 22 which are transmitted through, for example, control lines 72. Each of energy sources 12a, 12b and 12c pass optical energy through energy coupling lenses 14a, 14b and 14c respectively. Energy coupling lenses 14a, 14b and 14c focus optical energy on fiber optic bundles 20a, 20b and 20c through optical filters 16a, 16b and 16c respectively. In one embodiment of the present invention, optical filters 16 may include a plurality of selectable optical filters which may be selected by filter selection signals from control circuit 22 which are transmitted through, for example, control lines 70. The number of energy coupling lenses, optical filters and fiber optic bundles will depend upon the design of ablation system 15, however, the number of coupling lenses, optical filters and fiber optic bundles will generally correspond to the number of regions the ablation instrument is designed to separately heat within the body cavity being treated. In all other respects, the ablation system 15 illustrated in FIG. 3 is substantially identical to the ablation system 15 illustrated in FIG. 1.

Figure 4:
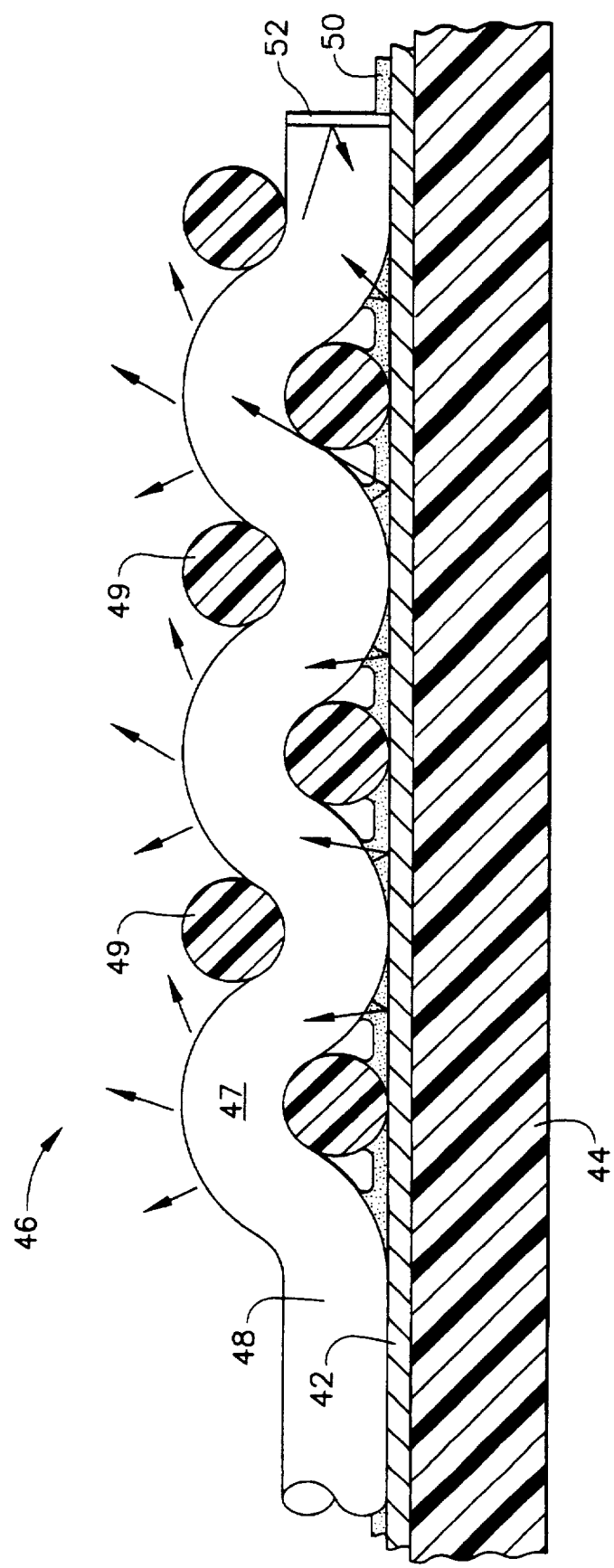
FIG. 4 is a cutaway view of a cross section of an expandable diffusing web according to the present invention.

FIG. 4 is a cutaway view of a cross section of an expandable diffusing web 46 according to the present invention. In FIG. 3 expandable defusing web 46 includes reflective coating 42, balloon 44, optical fiber mesh 47 and an adhesive layer 50 for attaching the fiber optic mesh to the balloon. Reflective coating 42 may be, for example, a coating of silver or other reflective material which covers the outer surface of Balloon 44. Balloon 44 may be constructed of, for example, mylar or other expandable balloon material. Optical fiber mesh 47 may include optical fibers 48, reflective fiber terminator 52 and fill threads 49. Fill threads 49 may be solid as illustrated in FIG. 4. Alternatively, fill threads 49 may be made of an optically conductive material. Optical fiber mesh 47 may be, for example, a light emitting woven light emitting panel which is manufactured by Ploy-Optic or by Lumitex. Reflective fiber terminator 52 is located at the end of optical fiber 48 to reflect any optical energy which reaches the end of optical fiber 48 without being diffused.

Figure 5:
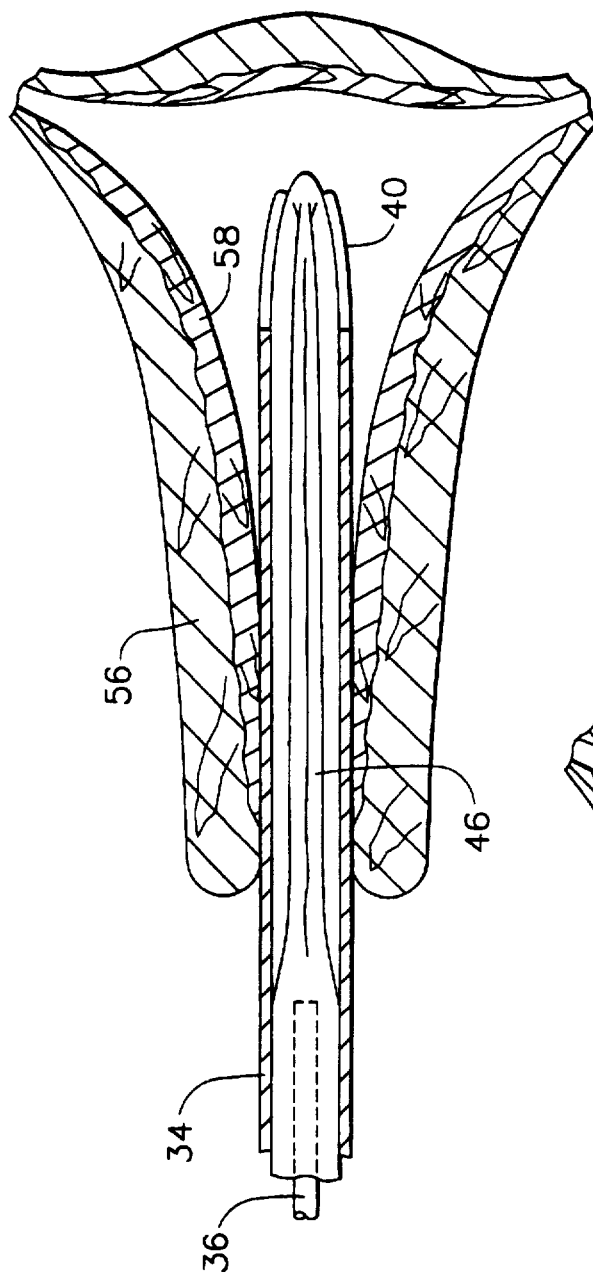
FIG. 5 is a cutaway side view of the distal end of the ablation instrument according to the present invention prior to deployment of the expandable diffusing web.

FIG. 5 is a cutaway side view of the distal end of ablation instrument 10 according to the present invention prior to deployment of expandable diffusing web 46. In FIG. 5, the distal end of rigid sleeve 34, including expandable diffusing web 46 is disposed within uterus 56. Expandable diffusing web 46 is folded to fit within rigid sleeve 34. The interior of uterus 56 is covered by an endometrial layer 58. As rigid sleeve 34 is withdrawn, by, for example moving sleeve retractor 32, expandable diffusing web 46 forces expandable sleeve tip 40 open, exposing expandable diffusing web 46. Fluid line 36 is connected to the proximal end of expandable diffusing web 46 such that a fluid, such as air, supplied at fluid source connector 29 fills the interior of expandable diffusing web 46, forcing expandable diffusing web 46 to expand.

Figure 6:
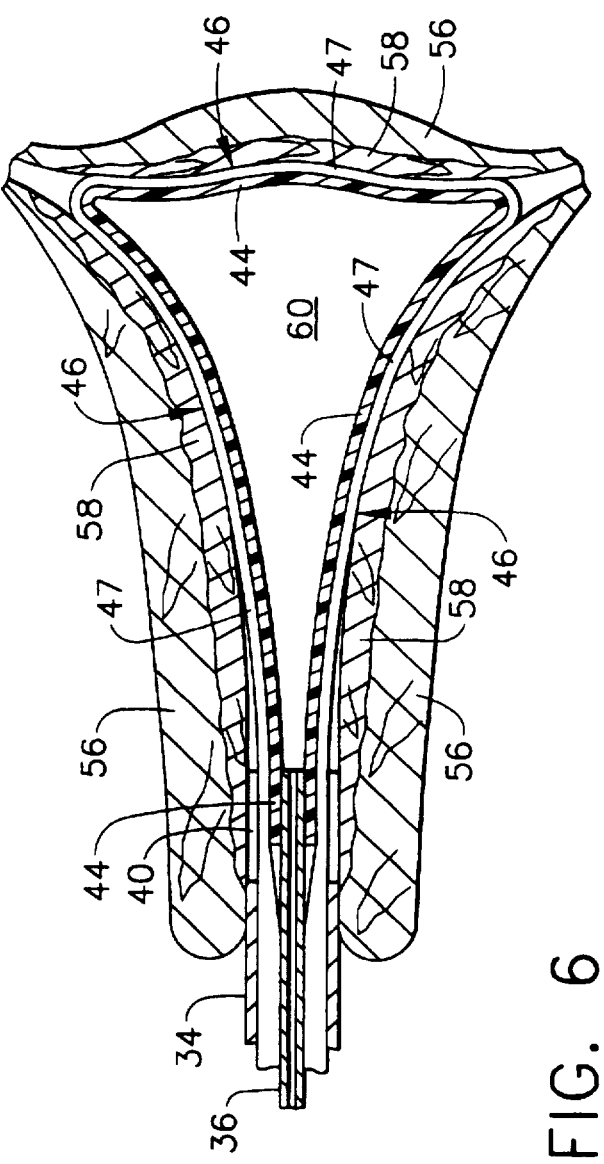
FIG. 6 is a cutaway side view if the distal end of the ablation instrument according to the present invention after deployment of the expandable diffusing web.

FIG. 6 is a cutaway side view if the distal end of ablation instrument 10 according to the present invention after deployment of expandable diffusing web 46. In FIG. 6, rigid sleeve 34 has been retracted, exposing expandable diffusing web 46. Expandable diffusing web 46, which includes balloon 44 and optical fiber mesh 47 is expanded to fit against endometrial lining 58 of uterus 56 by filling balloon interior 60 with a fluid such as air. Fluid line 46 connects balloon interior 60 to fluid source connector 29.

Figure 7:
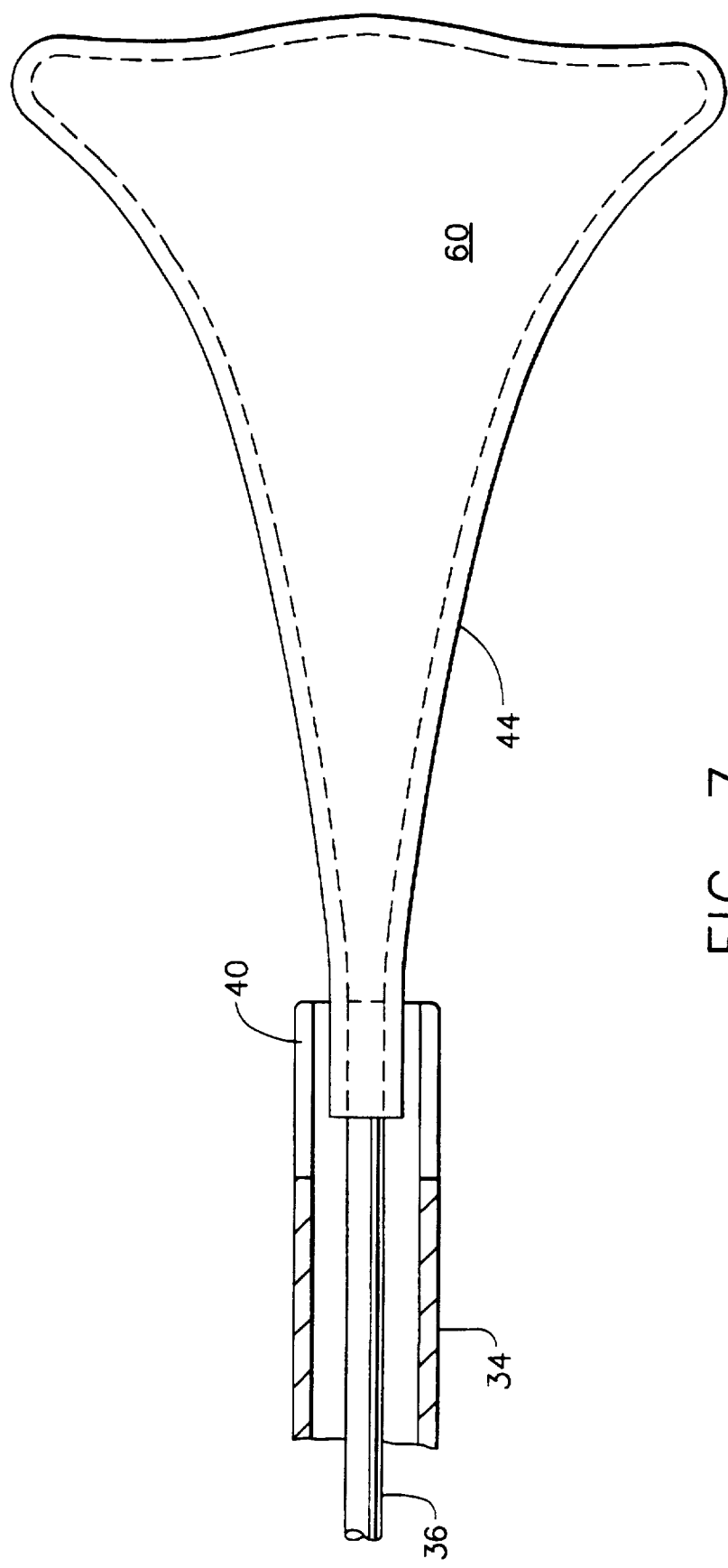
FIG. 7 is a side view of a balloon for use in the present invention.

FIG. 7 is a side view of a balloon 44 for use in the present invention. It will be recognized that balloon 44 may be shaped to fit within any body cavity, however, in the embodiment of the invention described herein, expandable diffusing web 46 is designed to be used within the uterus to destroy the endometrial lining. Thus, balloon 44 illustrated in FIG. 7 is shaped to fit within the uterus and to hold the optical fiber mesh firmly against at least a substantial portion of the endometrial lining. Nor is it necessary that the invention be limited to the use of a balloon as an expandable element since any means of expanding expandable diffusing web 46 to position optical fiber mesh near or adjacent the interior lining (e.g. the endometrium) of the body cavity to be treated is within the scope of the present invention. In FIG. 7, balloon 44 has been expand ed by filling interior 60 with an appropriate fluid, such as air, and the expanded balloon 44 takes on the shape of the interior of a uterus.

Figure 8:
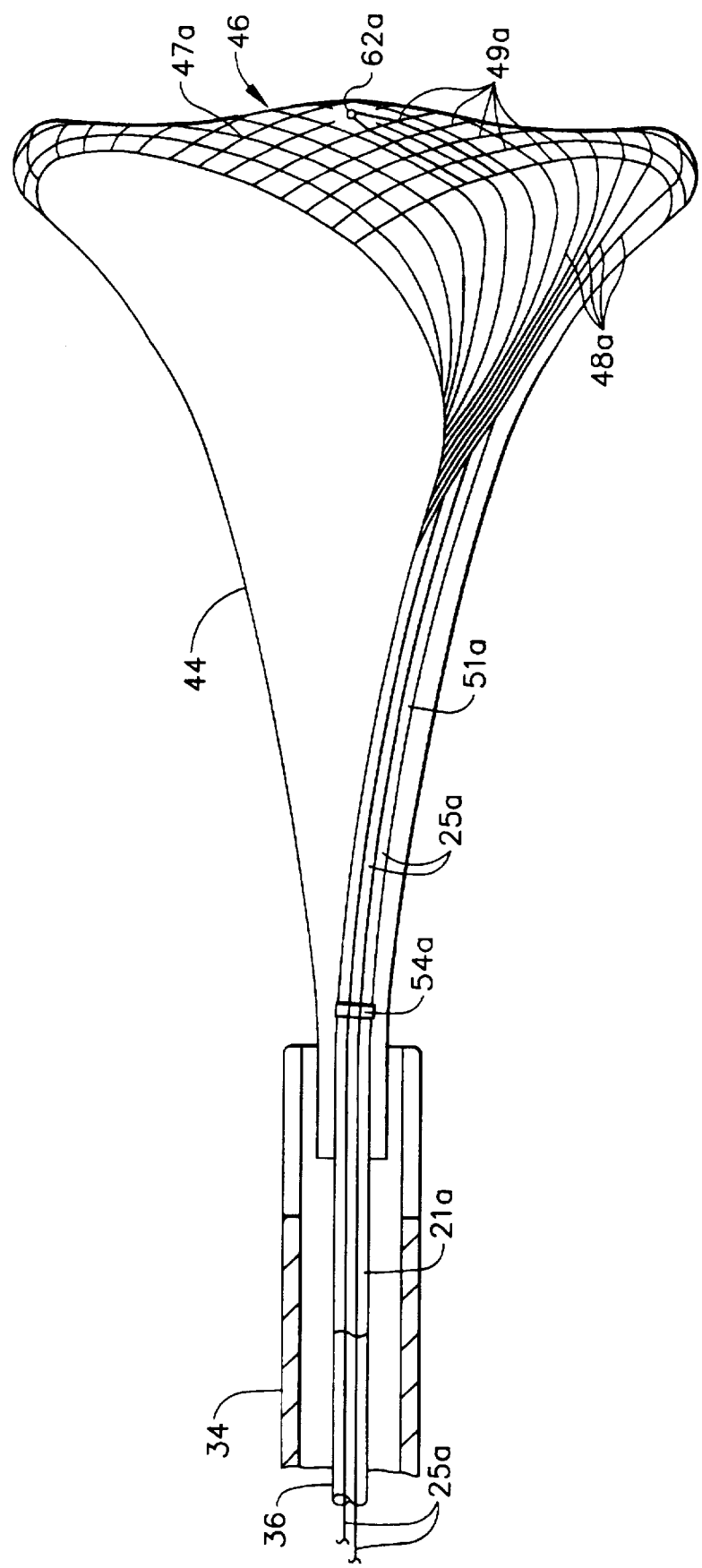
FIG. 8 is a side view of the distal end of the ablation instrument according to present invention illustrating a first optical fiber mesh with a first thermocouple.

FIG. 8 is a side view of the distal end of ablation instrument 10 according to the present invention illustrating a portion of expandable diffusing web 46 which includes a first optical fiber mesh 47a. The embodiment of the invention illustrated in FIG. 8 further includes a first thermocouple 62a. In FIG. 8, optical fiber mesh 47a is disposed on the distal end of balloon 44. In FIG. 8, optical fiber mesh 47a includes optical fibers 48a which are interwoven with fill threads 49a. At their proximal end, optical fibers 48a of optical fiber mesh 47a are connected to the distal end of one of fiber optic bundles 21 which extend through rigid sleeve 34, alternatively, optical fibers 48a of optical fiber mesh 47a may be a continuation of one of the optic fiber bundles 21. For example, the proximal ends of fiber optics 48a may be gathered together to form an optical fiber bundle 51a which is connected to, for example, the distal end of fiber optic bundle 21a using, for example a butt-connector such as the one used to connect fiber optic bundle 20a with fiber optic bundle 21a, alternatively, fiber bundle 51a may be a continuation of the distal end of fiber optic bundle 21a. Fiber optic bundle 21a is joined to or disperses to form optical fibers 48a such that optical energy is passed from fiber optic bundle 21a to optical fibers 48a, thus optical energy generated at optical energy source 12 may be transmitted through fiber optic bundle 20a to fiber optic bundle 21a and through fiber optic bundle 21a to optical fibers 48a of optical fiber mesh 47a. Thermocouple 62a is positioned to detect the temperature of tissue adjacent optical fiber mesh 47a. Temperature signal wires 25a, being connected to thermocouple 62a, relay a signal representative of the temperature at thermocouple 62a to temperature signal wires 24a which, in turn relay the signal to control circuit 22. Optical fiber mesh 47a, being positioned on balloon 44, is held in place against the tissue to be treated by the expansion of balloon 44 as a result of the fluid supplied through fluid line 36.

Figure 9:
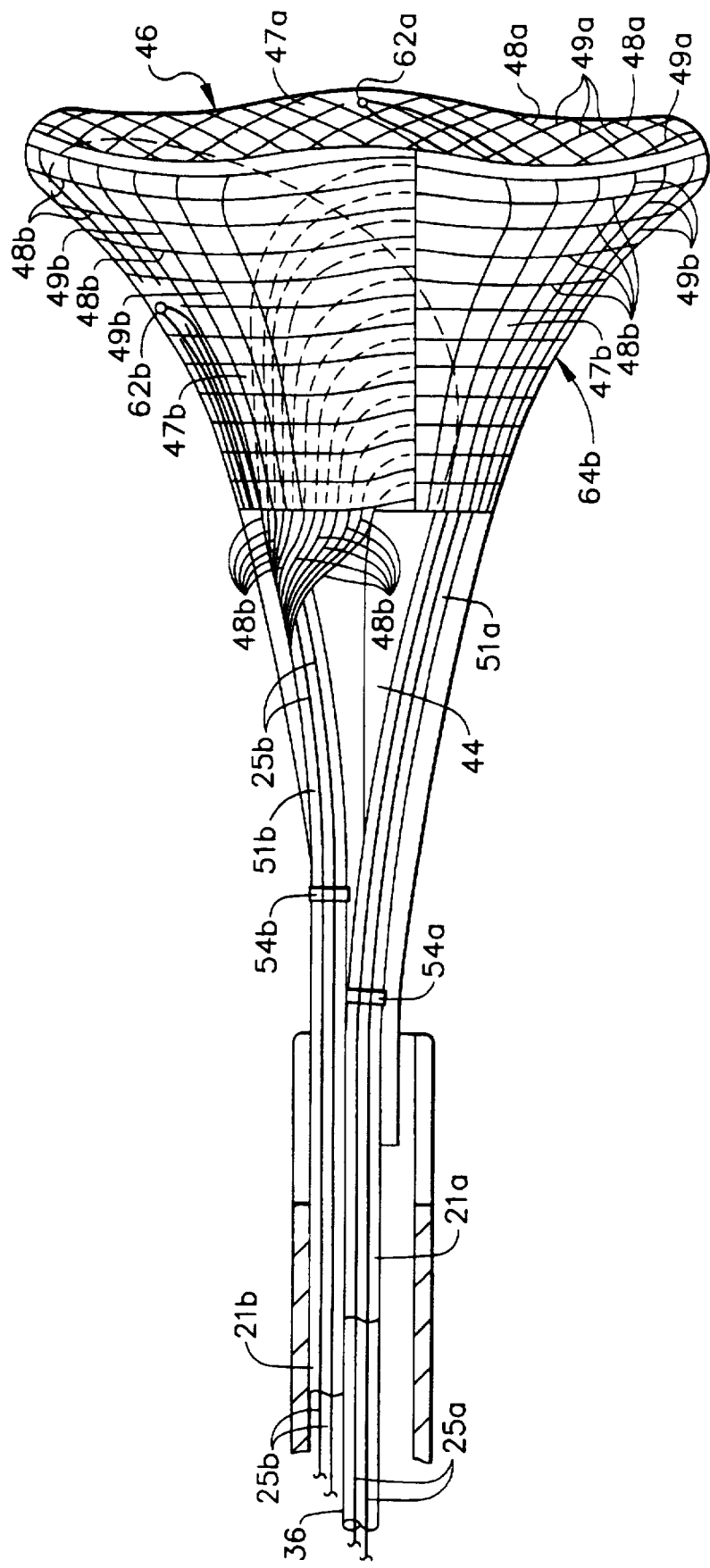
FIG. 9 is a side view of the distal end of an ablation instrument according to the present invention illustrating first and second heating element segments including first and second thermocouples.

FIG. 9 is a side view of the distal end of ablation instrument 10 according to the present invention illustrating a portion of expandable diffusing web 46 which includes a first optical fiber mesh 47a and a second optical fiber mesh 47b. The embodiment of the invention illustrated in FIG. 9 further includes a first thermocouple 62a and a second thermocouple 62b. In FIG. 9, a second optical fiber mesh 47b has been wrapped around the distal end of the balloon illustrated in FIG. 8 to increase the surface area of balloon 44 covered by optical fiber mesh 47. Thus, the previous description of the instrument with respect to FIG. 8 is applicable with respect to like elements of FIG. 9. In addition to the elements described with respect to FIG. 8. FIG. 9 illustrates optical fiber mesh 47b which includes optical fibers 48b which are interwoven with fill threads 49b. At their proximal end, optical fibers 48b of optical fiber mesh 47b are connected to the distal end of one of fiber optic bundles 21 which extend through rigid sleeve 34. For example, the proximal ends of fiber optics 48b may be gathered together to form an optical fiber bundle 51b which is connected to, for example, the distal end of fiber optic bundle 21b using, for example, a butt-connector such as the one used to connect fiber optic bundle 20b with fiber optic bundle 21b, alternatively, fiber bundle 51b may be a continuation of the distal end of fiber optic bundle 21b. Fiber optic bundle 21b is joined to optical fibers 48b such that optical energy is passed from fiber optic bundle 21b to optical fibers 48b, thus optical energy generated at optical energy source 12 may be transmitted through fiber optic bundle 20b to fiber optic bundle 21b and through fiber optic bundle 21b to optical fibers 48b of optical fiber mesh 47b. Thermocouple 62b is positioned on balloon 44 to detect the temperature of tissue adjacent optical fiber mesh 47b. Temperature signal wires 25b, being connected to thermocouple 62b, relay a signal representative of the temperature at thermocouple 62b to temperature signal wires 24b which, in turn, relay the signal to control circuit 22. Optical fiber mesh 47b, being positioned on balloon 44, is held in place against the tissue to be treated by the expansion of balloon 44 as a result of the fluid supplied through fluid line 36.

Figure 10:
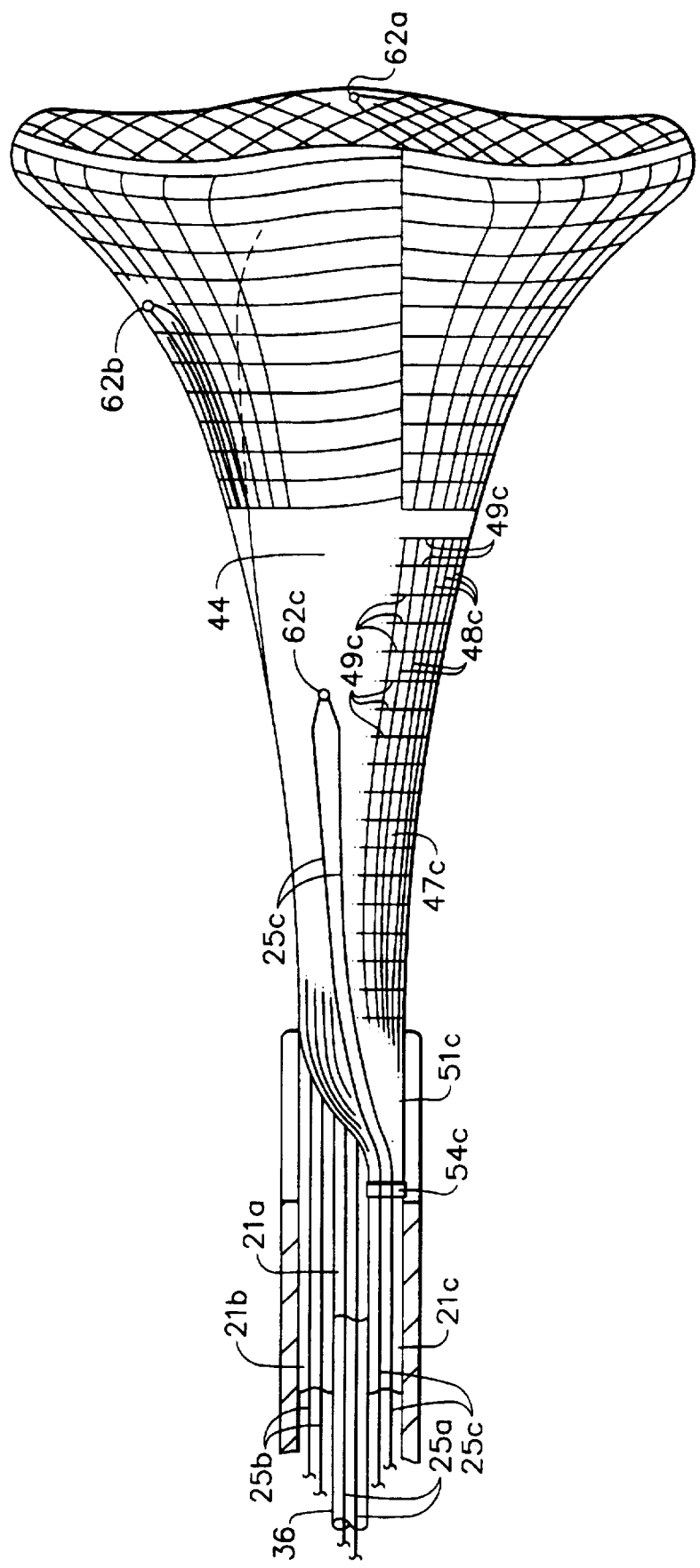
FIG. 10 is a side view of the distal end of an ablation instrument according to the present invention illustrating first, second and third heating element segments including first, second and third thermocouples.

FIG. 10 is a side view of the distal end of ablation instrument 10 according to the present invention illustrating a portion of expandable diffusing web 46 which includes a first and optical fiber mesh 47a, a second optical fiber mesh 47b and a third optical fiber mesh 47c. The embodiment of the invention illustrated in FIG. 10 further includes a first thermocouple 62a, a second thermocouple 62b and a third thermocouple 62c. In FIG. 10, a third optical fiber mesh 47c has been wrapped around the distal end of the balloon illustrated in FIG. 8 and FIG. 9 to increase the surface area of balloon 44 covered by optical fiber mesh 47. Thus, the previous description of the instrument with respect to FIG. 8 and FIG. 9 is applicable with respect to like elements of FIG. 10. In addition to the elements described with respect to FIG. 8 and FIG. 9, FIG. 10 illustrates an optical fiber mesh 47c which includes optical fibers 48c which are interwoven with fill threads 49c. At their proximal end, optical fibers 48c of optical fiber mesh 47c are connected to the distal end of one of fiber optic bundles 21 which extend through rigid sleeve 34. For example, the proximal ends of fiber optics 48c may be gathered together to form an optical fiber bundle 51c which is connected to, for example, the distal end of fiber optic bundle 21c using, for example, a butt-connector such as the one used to connect fiber optic bundle 20c with fiber optic bundle 21c, alternatively, fiber bundle 51c may be a continuation of the distal end of fiber optic bundle 21c. Fiber optic bundle 21c is joined to optical fibers 48c such that optical energy is passed from fiber optic bundle 21c to optical fibers 48c, thus optical energy generated at optical energy source 12 may be transmitted through fiber optic bundle 20c to fiber optic bundle 21c and through fiber optic bundle 21c to optical fibers 48c of optical fiber mesh 47c. Thermocouple 62c is positioned on balloon 44 to detect the temperature of tissue adjacent optical fiber mesh 47c. Temperature signal wires 25c, being connected to thermocouple 62c, relay a signal representative of the temperature at thermocouple 62c to temperature signal wires 24c which, in turn, relay the signal to control circuit 22. Optical fiber mesh 47c, being positioned on balloon 44, is held in place against the tissue to be treated by the expansion of balloon 44 as a result of the fluid supplied through fluid line 36.

The embodiment of the invention illustrated in FIG. 1 is adapted to controllably heat three separate regions within the uterus of a human patient to selectively destroy the endometrial layer within those regions. The energy and depth of penetration of the optical energy may be controlled by controlling the energy level and wavelength of the energy transmitted to the proximal end of each fiber optic bundle 20a, 20b and 20c. Longer wavelengths penetrate deeper into tissue. Shorter wavelengths, for example, blues and greens, may be used to achieve surface heating. Thus, depending on the effect that is desired, different wavelength of optical energy may be selected. Optical energy is transmitted through optical bundles 20 to optical bundles 21 and optical bundles 51. Optical energy which passes through optical bundles 51 is diffused by optical fiber mesh 47 of expandable diffusing web 46. Reflective coating 42 acts to reflect optical energy away from balloon 44 and into tissue surrounding expandable diffusing web 46. The depth of penetration of the optical energy into surrounding tissue will be a function of a number of factors, including the wavelength of the optical energy radiated by expandable diffusion web 46 and the distance from the expandable diffusion web 46 to the tissue to be treated. The rate at which the tissue is heated will also depend upon a number of factors, including the output energy generated by optical energy source 12, the losses in electro-optic generator 11 and ablation instrument 10, the distance from the expandable diffusion web 46 to the tissue to be treated and the wavelength of the optical energy. However, by monitoring the tissue as it is treated using, for example, thermocouples 62, the surgeon may control the temperature of the tissue being treated with relative accuracy.

In use a surgeon will introduce the distal end of ablation instrument 10 into the body cavity of a patient such that expandable sleeve tip 40 is positioned at a predetermined depth within the body cavity. For the purposes of this discussion, the body cavity to be treated will be the uterus of a female human being. It will be recognized that, with slight modification, the present invention may be used to treat other body cavities. Once sleeve tip 40 is inserted into the uterus 56 as illustrated in FIG. 5, sleeve retractor 32 may be used to slide rigid sleeve 34 back away from expandable diffusing web 46. As rigid sleeve 34 is retracted, expandable diffusing web 46 forces expandable sleeve tip 40 open. Once sleeve retractor 32 reaches its proximal most travel point it is stopped by sleeve retractor stop 33 which prevents rigid sleeve 34 from retracting further. Once rigid sleeve 34 is retracted, expandable diffusing web 34 may be expanded to contact the interior of the uterus by, for example inflating balloon 44 by injecting an appropriate fluid, such as, for example air into balloon interior 60. Fluid is introduced into balloon 44 through fluid line 36 which is connected to fluid source connector 29 which, in the embodiment illustrated in FIG. 1, is connected to a syringe and plunger which may be used to inflate or deflate balloon 44. Expandable diffusing web 46, being shaped to fit the body cavity, e.g. the uterus, being treated, is designed to force optical fiber mesh 47 against a substantial portion of the interior surface of the body cavity. Thus, when expandable diffusing web 46 is fully expanded, optical fiber mesh 47 is positioned directly adjacent or in direct contact with endometrium 58 of uterus 56.

Once expandable diffusing web 46 is positioned within uterus 56, optical energy may be supplied to optical fiber mesh 47 by turning on optical energy source 12. Once optical energy source 12 is turned on, the light radiated by optical energy source 12 is focused on the proximal end of optical fiber bundle 20 by energy coupling lens 14. As optical energy passes through optical filter 16, it is filtered to remove unwanted wavelengths. As optical energy passes through variable attenuator 18 the energy level is attenuated. Therefore, the optical energy focused upon fiber optic bundle 20 is filtered and attenuated such that it is optical energy of a selected wavelength and energy level. Optical energy focused upon the proximal end of fiber optic bundle 20 is transmitted through fiber optic bundle 20 to fiber optic bundle 21 and from fiber optic bundle 21 to expandable diffusing web 46 where it is radiated into the endometrial layer from optical fiber mesh 47. Where different optical energy levels or wavelengths are to be transmitted to different regions of the endometrium, a plurality of energy coupling lenses 14a–14c, optical filters 16a–16c and variable attenuators 18a–18c may be used to focus filtered optical energy onto a plurality of fiber optic bundles 20a–20c as illustrated in FIG. 1. Alternatively, where different optical energy levels or wavelengths are to be transmitted to different regions of the endometrium, a plurality of optical energy sources 12a–12c, energy coupling lenses 14a–14c and optical filters 16a–16c may be used to focus filtered optical energy onto a plurality of fiber optic bundles 20a–20c as illustrated in FIG. 2. The optical energy focused on optical bundles 20a–20c may then be transmitted through optical fiber bundles 21a–21c to each optical fiber mesh 47a–47c.

Once the optical energy reaches expandable diffusing web 46, it is radiated by optical fibers 48 which are woven with fill threads 49 to form optical fiber mesh 47. Radiation from optical fibers 48 which is not directed into the tissue adjacent optical fiber mesh 47 is reflected by reflective coating 42 as illustrated in FIG. 4. Thus, both the energy radiated toward the tissue and the reflected energy is absorbed by the tissue adjacent to fiber optic mesh 47. Further, since the energy is transmitted optically, it is not necessary for the tissue to be directly adjacent fiber optic mesh 47 as the radiated energy will be absorbed by any tissue illuminated by the energy from the mesh. This arrangement provides for uniform escape or emission of energy focused on the fiber optic bundles 20 in fiber optic generator 11. Further, in an arrangement according to the present invention, energy is evenly radiated from the outside of the expandable diffusing web, and is, therefore absorbed by the endometrial lining of the uterus causing temperature of the tissue to rise.

Figure 11:
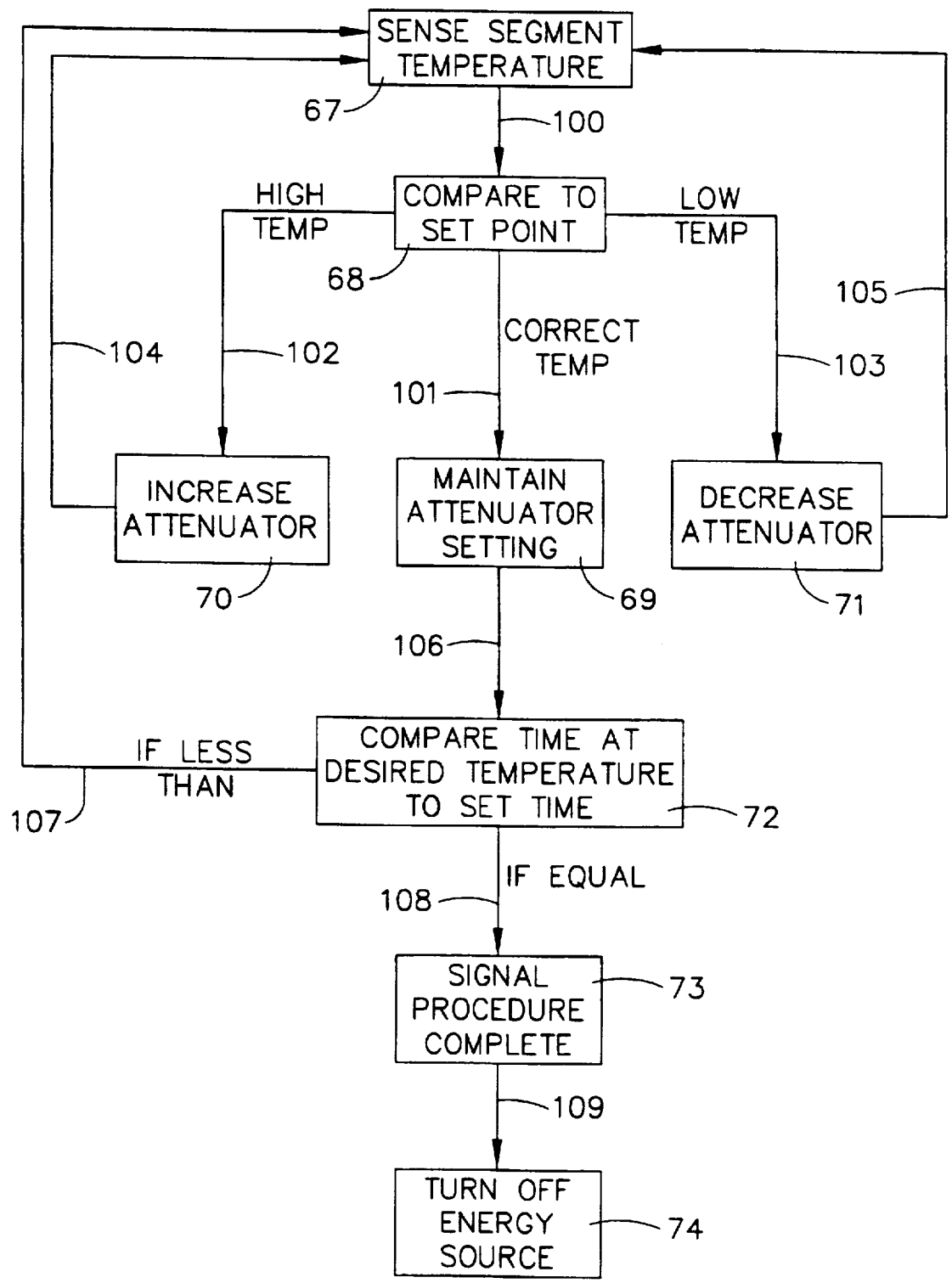
FIG. 11 is a flow diagram illustrating one embodiment of the control flow for the electro-optic circuitry for an ablation instrument according to the present invention.

The control sequence for control circuit 22 of the electro-optic generator illustrated in FIG. 1 is illustrated in FIG. 11. Once expandable diffusing web 46 has been positioned and inflated as described previously, optical energy may be supplied to expandable web 46 to heat endometrial lining 58. The first step in supplying optical energy to endometrial lining 58 is to select an appropriate wavelength. In particular, red and near infrared wavelengths would be selected for heating deep (e.g. 0–10 millimeters) into uterine tissue. Ultraviolet, blue or green wavelengths would be used for heating uterine tissue to a depth of, for example, (0–3 millimeters). Once the appropriate optical energy wavelength has been selected by, for example, adjustment of optical filter 16 or by appropriate selection of optical energy source 12, optical energy may be supplied to expandable web 46. The energy level or intensity of the optical energy supplied to expandable web 46 may be controlled by controlling the attenuation of variable attenuators 18 or by controlling the intensity of optical energy source 12. Temperature feedback from thermocouple 62 may be used to adjust the energy level supplied to fiber optic bundles 20. Thus, the temperature of the body lining being treated is controlled by controlling the energy level supplied to expandable web 18 while the depth of penetration of the energy supplied to expandable web 46 is controlled by controlling the wavelength of the optical energy supplied to fiber optic bundles 20.

The flow diagram of FIG. 11 illustrates the control sequence for the electro-optic generator illustrated in FIG. 1. The temperature of endometrial lining 58 is sensed by, for example, thermocouple 62 which provides a signal to control circuit 22 through temperature signal wires 24 and 25. As illustrated in FIG. 11, control circuit 22, in step 67, senses the temperature at thermocouple 62 and produces a signal 100 which is representative of the temperature measured at thermocouple 62. In step 68, signal 100 is compared to a predetermined set point temperature such as, for example, any temperature between 42° C. and 100° C. for a time sufficient to destroy the inner lining of the organ in question. If the temperature represented by signal 100 is lower than the set point temperature, control circuit 22 generates a signal 103. In step 71, signal 103 causes control circuit 22 to decrease the attenuation of the optical energy focused on optical fiber bundle 20, thus increasing the optical energy supplied to expandable web 46. Once the attenuation has been reduced, control circuit 22 generates a signal 105 which causes control circuit 22 to return to step 67 where the temperature is measured again and a new signal 100 is generated. Once the temperature represented by signal 100 reaches the set point temperature control circuit 22, in step 69, generates a signal 106 which is representative of the time the endometrium has been at the desired temperature. The time represented by signal 106 is compared, in step 72 to a predetermined set time and if the time represented by signal 106 is less than the predetermined set time, control circuit 22 generates signal 107 which returns control circuit 22 to step 67. If during the control cycle, the signal 100 rises above the set point temperature, then signal 102 is generated, causing control circuit 22 to increase attenuation at variable attenuators 18, thus decreasing the optical energy delivered to expandable diffusing web 46. Once the actual time at the desired temperature, represented by signal 106, reaches the predetermined set time in step 72, signal 108 is generated indicating, in step 73, that the procedure is complete and generating signal 109 which turns off optical energy source 12 in step 74.

Figure 12:
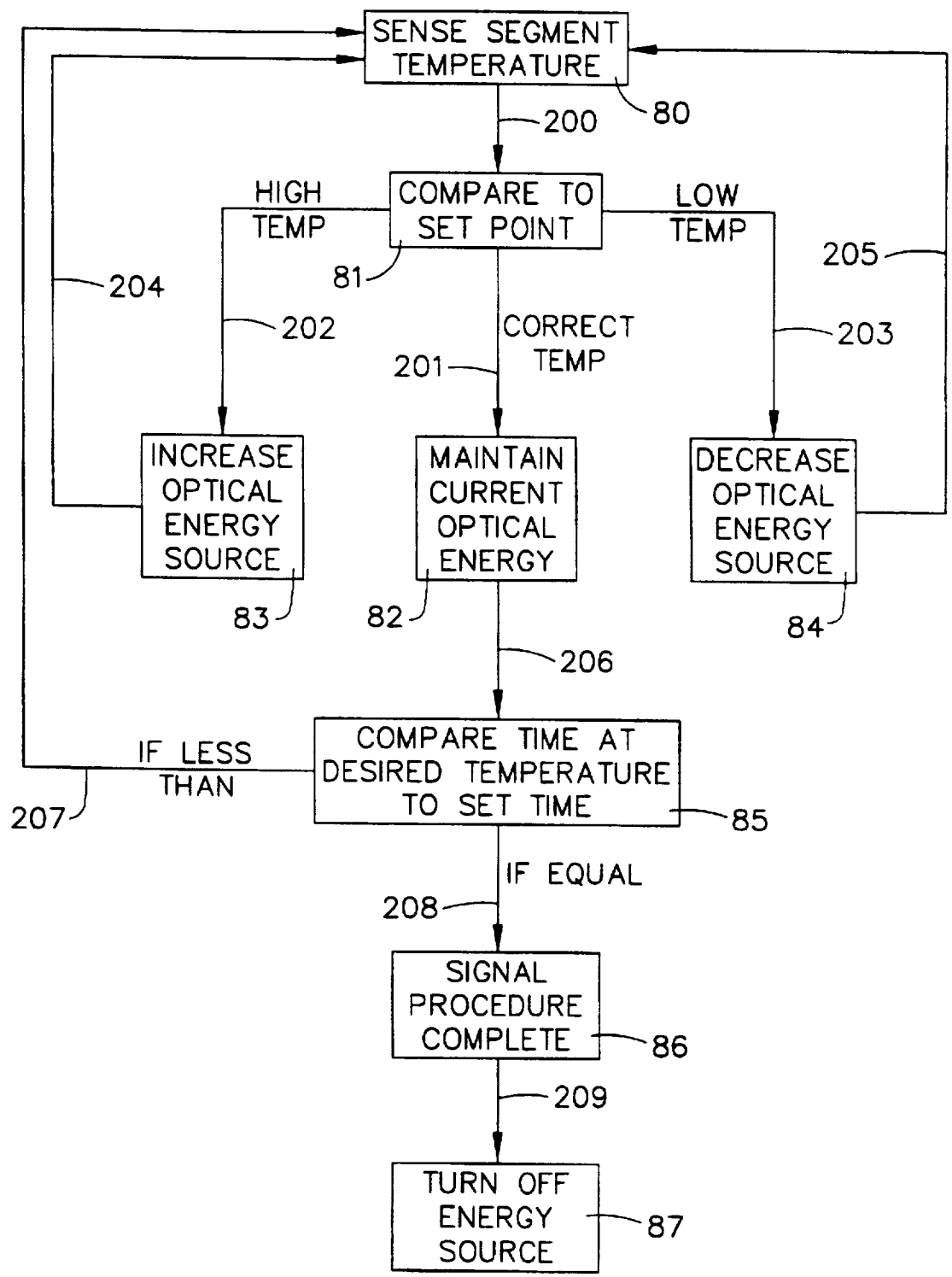
FIG. 12 is a flow diagram illustrating one embodiment of the control flow for the electro-optic circuitry for an ablation instrument according to the present invention.

The flow diagram of FIG. 12 illustrates the control sequence for the electro-optic generator illustrated in FIG. 2. The temperature of endometrial lining 58 is sensed by, for example, thermocouple 62 which provides a signal to control circuit 22 through temperature signal wires 24 and 25. As illustrated in FIG. 12, control circuit 22, in step 80, senses the temperature at thermocouple 62 and produces a signal 200 which is representative of the temperature measured at thermocouple 62. In step 81, signal 200 is compared to a predetermined set point temperature. If the temperature represented by signal 200 is lower than the set point temperature, control circuit 22 generates a signal 203. In step 84, signal 203 causes control circuit 22 to increase the optical energy from optical energy source 12 which increases the intensity of the optical energy focused on optical fiber bundle 20, thus increasing the optical energy supplied to expandable web 46. Once optical energy has been increased, control circuit 22 generates a signal 205 which causes control circuit 22 to return to step 80 where the temperature is measured again and a new signal 200 is generated. Once the temperature represented by signal 200 reaches the set point, temperature control circuit 22, in step 82, generates a signal 206 which is representative of the time the endometrium has been at the desired temperature. The time represented by signal 206 is compared, in step 85 to a predetermined set time and, if the time represented by signal 206 is less than the predetermined set time, control circuit 22 generates signal 207 which returns control circuit 22 to step 80. If during the control cycle, the signal 200 rises above the set point temperature, then signal 202 is generated, causing control circuit 22 to decrease the optical energy from optical energy source 12, which decreases the intensity of the optical energy focused on optical fiber 20, decreasing the energy delivered to expandable diffusing web 46. Once the actual time at the desired temperature, represented by signal 206, reaches the predetermined set time in step 85, signal 208 is generated indicating, in step 86, that the procedure is complete and generating signal 209 which turns off optical energy source 12 in step 87.

In operation, ablation instrument 10 would be connected to electro-optic generator 11 and the distal end of instrument 10 would be inserted into the appropriate body organ, for example, into the uterus 56. Rigid sleeve 34 would then be retracted using sleeve retractor 32, thereby exposing expandable diffusing web 46 which includes balloon 44. Balloon 44 is inflated using, for example, balloon inflator syringe 30 which includes plunger 30. Once balloon 44 is inflated forcing expandable diffusing web 46 to conform to the interior of uterus 56, electro-optic generator 11 is activated, thus delivering optical energy to optical fibers 48 of optical fiber mesh 47 on expandable diffusing web 46. Control circuit 22 is then used to monitor the heating of endometrial layer 58 of uterus 56 through thermocouple(s) 62. Control circuit 22 acts to bring endometrial layer 58 up to a desired temperature, hold endometrial layer 58 at that temperature for a predetermined length of time and then turn off optical energy to the endometrial layer. Expandable diffusing web 46 may then be collapsed by deflating balloon 44 using, for example syringe 30. Once expandable diffusing web 46 is deflated, it may be retracted from uterus 56.

Use of an ablation instrument according to the present invention may be advantageous, when compared to electro-surgical or other apparatus for use in endometrial ablation, for example: Light energy may be less likely to interfere with the operation of the thermocouples; a light diffusing fiber-optic web may be more adaptable to expansion than RF electrodes; contact with the uterine wall is not required as it may be in an RF device; it is possible to control the depth of heating by controlling the wavelength of the optical energy applied to the endometrial lining.

According to one embodiment of the present invention, light energy from optical energy source 12, which may be, for example, common projection lamps, may be used to uniformly heat the endometrium 58° to 70° C. and thereby ablate the endometrium. The array of fiber-optic mesh or webs 47 are connected individually to an array of high intensity lamps 12 via fiber-optic cables 20 and 21. Fiber optic mesh 47 may Heating of the endometrium 58 is achieved through absorption of the optical radiation transmitted through fiber optic cables 20 and 21. The temperature of each fiber optic web, for example fiber optic webs 47a–47c, is monitored by a thermocouple, for example 62a–62c, which, through a feedback loop including temperature signal wires 24 and 25 which are connected to control circuitry 22, controls the intensity of its associated lamp 12. In this embodiment, fiber-optic mesh 47 and thermocouples 62 cover the outside of an inflatable silvered mylar pouch or balloon 44. Balloon 44 is inserted into the uterus and then inflated. Inflation brings fiber-optic webs 47 and thermocouples 62 into contact with the endometrium or endometrial layer 58. Lamps 12 are then turned on and the temperature of the endometrium is monitored intensity of the optical energy supplied to fiber optic webs 47 is controlled by monitoring feedback from thermocouples 62 until therapy is complete. The silvered surface of mylar balloon 44 directs all the optical radiation into the endometrium for heating.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. An apparatus for heating the inner lining of an organ, said apparatus comprising:

an expandable element wherein said expandable element has an interior surface and an exterior surface and said exterior surface of said expandable element is covered by an optically reflective coating;

an optically conductive diffusing material on said expandable element wherein said optically conductive diffusing material comprises a web of optical fibers;

a light source connected to said optically conductive material by one or more optical conductors.

2. An apparatus for heating the interior of an organ, said apparatus comprising:

an expandable element wherein said expandable element has an interior surface and an exterior surface and said exterior surface is covered, at least in part, by an optically reflective layer;

an optically conductive diffusing material on said expandable element wherein said optically conductive diffusing material comprises a web of optical fibers;

a light source connected to said optically conductive diffusing material by one or more optical conductors wherein said light source comprises one or more lamps;

one or more temperature sensors on said expandable element wherein said one or more temperature sensors comprise thermocouples.

3. An apparatus according to claim 2 wherein said expandable element includes a web of optical fibers surrounding a balloon.

* * * * *